United States Patent [19]

Harper

[11] Patent Number: 6,010,390
[45] Date of Patent: Jan. 4, 2000

[54] CROP POLLINATION METHOD BY INSECTS

[76] Inventor: William A. Harper, 16541 Redmond Way #140C, Redmond, Wash. 98052-4463

[21] Appl. No.: 09/100,773

[22] Filed: Jun. 8, 1998

[51] Int. Cl.[7] .................................................. A01K 67/033
[52] U.S. Cl. ...................................................... 449/2; 449/1
[58] Field of Search ............................ 449/1, 2; 119/6.5, 119/6.6

[56] References Cited

U.S. PATENT DOCUMENTS

| | | |
|---|---|---|
| 3,893,420 | 7/1975 | Andreev et al. . |
| 3,936,894 | 2/1976 | Barber . |
| 4,075,783 | 2/1978 | Burden et al. ........................... 449/2 X |
| 4,293,966 | 10/1981 | Weiderrich . |
| 4,319,371 | 3/1982 | Weiderrich . |
| 4,365,372 | 12/1982 | Norman . |
| 4,411,220 | 10/1983 | Voegele et al. . |
| 4,491,994 | 1/1985 | Youssef . |
| 4,594,964 | 6/1986 | Vargas et al. . |
| 4,628,558 | 12/1986 | Pederson . |
| 4,716,609 | 1/1988 | Norman . |
| 4,765,007 | 8/1988 | McCarthy . |
| 4,765,274 | 8/1988 | Pizzol et al. . |
| 5,113,799 | 5/1992 | Carr et al. . |
| 5,178,094 | 1/1993 | Carr et al. . |
| 5,277,647 | 1/1994 | Earl ............................................. 449/2 |
| 5,351,643 | 10/1994 | Hughes . |
| 5,403,226 | 4/1995 | Trafford . |
| 5,591,063 | 1/1997 | McCarthy . |
| 5,618,220 | 4/1997 | Mills . |

FOREIGN PATENT DOCUMENTS

| 1386127 | 4/1988 | Russian Federation ................... 449/1 |
|---|---|---|

OTHER PUBLICATIONS

Batra, S. W. T. (1982), The Hornfaced bee for Efficient Pollination of Small Farm Orchard; In Kerr, W. H. and L. V. Knutson (eds.), *Research for Small Farm, USDA Miscellaneous Publ.*, No. 1422; pp. 117–120.
Batra, S. W. T. (1984), Solitary Bees; *Scientific American*; 250 (2): 86–93.
Buchmann, S. L. and G. P. Nabhan (1996), *The Forgotten Pollinators*; Island Press, Washington, D.C.; pp. 131–143.
Free, J. B. (1993), *Insect Pollination of Crops*; 2nd ed., London, Academic Press; pp. 84–95.
Goerzen, D. W. (1992), Paraformaldenhyde Fumigation of Alfalfa Leafcutting Bee Nest *Material; Saskatchewan Agric. Development. Fund*, ISBN 0–88656–556–1.
Griffin, B. L. (1993), *The Orchard Mason Bee*; Knox Cellars, Bellingham, WA; pp. 1–54.
Kuhn, E. D. and J. T. Ambrose (1984), Pollination of Delicious Apple by Megachilid Bees of the Genus Osmia; *J. Kansas Ent. Soc.; 57*: 169–180.
Mayer, D. F. (1988), Effects of Dipping Alfalfa Leaf–cutting Bee Nesting Materials on Chalkbrood Disease; *Applied Agric. Res.;* 3: 167–169.
Mayer, D. F. (1990), Effects of Fungicides on Chalkbrood Diseases of Alfalfa Leafcutting Bee; *Applied Agriculture Research*; 5 (3): 223–226.

Murrelll, D. C. (1997), Alfalfa Seed and Leafcutter Bee Production in Saskatchewan; *Saskatchewan Agriculture and Food, Extension Bulletin*. No. 97–01.
Peterson, S. S. et al (1992), Current Status of the Alfalfa Leafcutting Bee; *Bee Science*; 2: 135–142.
Proctor, M. et al (1996), *The Natural History of Pollination*; Harper–Collins, London; pp. 99–125, 350–364.
Torchio, P. F. (1981a), Field Experiments with Osmia lignaria Propinqua Cresson as Pollinator in Almond Orchards; *J. Kansas Ent. Soc.*; 54 (4): 815–823.
Torchio, P. F. (1981b),.Field Experiments with Osmia lignaria propinqua Cresson as a Pollination in Almond Orchards; *J. Kansas Ent. Soc.*; 54 (4): 824–826.
Torchio, P. F. (1987), Use of Non–honey Bee Species as a Pollinator of Crops; *Ent. Soc. Ontario*; 118: 111–124.
Torchio, P. F. (1991), Use of Osmia lignaria propinqua as a Mobile Pollinator of Orchard Crops; *Envir. Entomol*; 20 (2): 590–596.
Torchio, P. F. (1992), Effects of Spore Dosage and Temperature on Pathogenic Expressions of Chalkbrood Syndrome Caused by Ascosphaera torchioi within Larvae of Osmia lignaria propinqua; *Envir. Entomol.*; 21 (5): 1086–1091.
Waters, N. D. (1971), Insect Enemies of the Alfalfa Leafcutting Bee and Their Control; *Univ. of Idaho, Current Information Series*, No. 163.
Batra, S. W. T. (1982), The Hornfaced bee for Efficient Pollination of Small Farm Orchard; In Kerr, W. H. and L. V. Knutson (eds.), Research for Small Farm, USDA Miscellaneous Publ., 1422, 117–120.
Batra, S. W. T. (1984), Solitary Bees, Scientific American; 250(2), 86–93.
Buchmann, S. L. and G. P. Nabhan (1996), The Forgotton Pollinators; Island Press, Washington, D.C.
Free, J. B. (1993), Insect Pollination of Crops; 2nd ed., London, Academic Press.
Goerzen, D. W. (1992), Paraformaldenhyde Fumigation of Alfalfa Leafcutting Bee Nest Material; Saskatchewan Agric. Deve. Fund, ISBN 0–88656–556–1.
Griffin, B. L. (1993), The Orchard Mason Bee; Knox Cellars, Bellingham, WA.
Kuhn, E. D. and J. T. Ambrose (1984), Pollination of Delicious Apple by Megachilid Bees of the Genus Osmia; J. Kansas Ent. Soc., 57, 169–180.
Mayer, D. F. (1988), Effects of Dipping Alfalfa Leaf–cutting Bee Nesting Materials on Chalkbrood Disease; Applied Agric. Res., 3, 167–169.

(List continued on next page.)

*Primary Examiner*—Robert P. Swiatek

[57] ABSTRACT

A new pollination method for efficient crop pollination by insects, primarily the economical production of solitary bees and other pollinating insects in such sufficient and reliable numbers so as to permit their timely distribution among and pollination of entomophilous plants to produce a crop. The process utilizes a clean manufacturing environment to rear insect ovum to imagoes that are isolated from agents of disease, predation, and parasitism. This pollination method employs a point-to-point distribution system that also substantially reduces material, handling, and shipping costs.

20 Claims, No Drawings

OTHER PUBLICATIONS

Murrelll, D. C. (1997), Alfalfa Seed and Leafcutter Bee Production in Saskatchewan; Saskatchewan Agriculture and Food, Extension Bul. No. 97–01.

Peterson, S. S. et al (1992), Current Status of the Alfalfa Leafcutting Bee; Bee Science, 2, 135–142.

Proctor, M. et al (1996), The Natural History of Pollination; Harper–Collins, London.

Torchio, P. F. (1981), Field Experiments with Osmia lignaria Propinqua Cresson as Pollinator in Almond Orchards; J. Kansas Ent. Soc., 54, 815–823.

Torchio, P. F. (1987), Use of Non–honey Bee Species as a Pollinator of Crops; Ent. Soc. Ontario, 118, 111–124.

Torchio, P. F. (1991), Use of Osmia lignaria propinqua as a mobile Pollinator of Orchard Crops; Envir. Entomol, 20–2, 590–596.

Torchio, P. F. (1992), Effects of Spore Dosage and Temperature on Pathogenic Expressions of Chalkbrood Syndrome Caused by *Ascosphaera torchioi* within Larvae of Osmia lignaria propinqua, Envir. Entomol.; 21–5, 1086–1091.

Waters, N. D. (1971), Insect Enemies of the Alfalfa Leafcutting Bee and Their Control; Univ. of Idaho, Current Information Series No. 163.

CROP POLLINATION METHOD BY INSECTS

BACKGROUND OF THE INVENTION

1. Field of the Invention

This invention discloses a new process for the efficient pollination of crops by insects, primarily the production of pollinating insects in sufficient and reliable numbers so a timely introduction of these pollinating insects among flowering plants produces a crop.

2. Background Art

Plant pollination by the honeybee (*Apis mellifera*) is by far the most commonly recognized means of crop pollination throughout the world. This pollination method depends on a single key element in the honeybee's natural history, this insect's social characteristics which give rise to the beehive. Because the beehive is the essential center of the any honeybee's existence the entire hive of 20,000 to 40,000 bees can be controlled by manipulation of the hive such as physically moving it about to pollinate crops. In the United States about two million honeybee hives are transported around the county each year in a migratory pattern that follows the bloom of those crops that benefit from pollination. Tractor-trailer rigs with one to two thousand hives move north and south with forklifts in tow to load and unload the heavy pallets stacked with hives. They move from freeway to county road to orchard or field to place their hives for a few days before reloading and moving on to the next contract location. Disruptions to a smooth flow of business by accidents, weather, and other such delays are common. A muddy field often restricts the optimum placement of unwieldy hives throughout an orchard or prevents their removal when scheduled. A single hive weights 37 to 54 kilograms (80 to 120 pounds) and occupies about 0.25 cubic meters (9 cubic feet), filled with bees they are an unstable load even in good conditions. Wet, cold weather in a region frequently delays the need for the hives for weeks and given that the beekeeper has future contracts already scheduled the hives are pulled early to honor the next location's contract requirements before the current contract's needs are fully met. Alternatively the next region is experience warm, sunny weather and the bloom is well advanced before the hives arrive from their last contract site. Such circumstances lead to inevitable contract disputes and conflicts between parties. Equally disruptive is the time dependent necessity of the grower to employ pesticides to prevent crop damage. While the honeybees are flying the application of many pesticides means death to them and the destruction of their hives; the beekeeper's livelihood can be wiped out by one bad application even by an application in a nearby field not even the subject of the contract. Application of pesticides and the destruction of hives are another continual source of conflict between beekeepers and the growers. The honeybee and its migratory hive are vulnerable to many uncontrollable operational circumstances.

The most vexing current challenge facing beekeepers is with the bees themselves, specifically diseases and pests within the hives. With the advent of the tracheal (*Acarapis woodi*) and varroa (*Varroa jacobsoni*) mites in the United States in the 1980's, together with past highly destructive diseases such as foulbrood, the modern hive is only kept alive through continuous applications of powerful medications. Despite these efforts the USDA Bee Research Laboratory in Beltsville, Md. has charted a 25% decline in the nation's population of managed honeybee hives in just the last decade. Disease and related problems have become so rampant that states have formulated regulations against entry of diseased and pest ridden hives. However, the laws are essentially unenforceable given the manner in which the hive loads are transported (huge compact loads of stinging bees, under netting, in the dark, on tight schedules), the availability of trained personnel to diagnose problems (no funding, no recourse), and the overwhelming absolute need for bees to pollinate crops. Despite the best intentions of many parties the requirement for pollination supercedes concerns over the spread of bee diseases, parasites, and predators. From the hive the free-roaming workers come and go from the fields gathering honey and pollen, sharing the field's bounty with other bees from other places; this free interaction also brings to the hives diseases, predators and parasites which establish themselves within the structure and their populations. The incessant flow of hives around the nation carries within it a reservoir of disease and pestilence continually infecting and re-infecting the hives of other colonies also joining the migration. Additionally, local hives in the migration's path are infected, as are the natural bees of the region such as solitaries who have little natural defense against such an assault. Near extinction of native solitaries, semi-solitaries and feral social bees has occurred in much of North America due to diseases, pests, habitat fragmentation and pesticides; Buchmann and Nabhan, 1996). Further, the twin practices of heavy medication and hive migration are giving rise to new antibiotic resistant bacterial infections and viruses which are being quickly dispersed by the finest highway system in the world. Yet the honeybee hive migration continues because pollination is a necessity to the orchardist and farmer raising any of the over ninety United States crops significantly benefiting from commercial honeybee pollination. The grower's economic survival is simply at issue. And no less a demand comes from the consuming public whose every third mouthful of food is dependent on pollination.

Modern agricultural practice requires the intensive cultivation of the land for a massive single crop to be an economically viable operation, the migratory hive pollination system is simply a workable response to this requirement. Hives are brought to the apple orchard or sunflower field to perform a single vital service over a few days time and then must be removed for the continued cultivation of the crop. If the hives remained they would either be poisoned by insecticides or shortly starve to death because no forage is available after the crop flowering is complete. Given no viable alternative pollination system the honeybee hive developed to supply honey has been drafted into use as the migrating pollination component within the manufacturing system of modern agriculture. The honeybee hive has become a necessary tool used once annually and sent away until needed a year hence. But the honeybee and its hive are organic, active organisms with continual significant demands which poorly adapt to quick, heavy uses followed by long-term storage. The fit of the honeybee hive for pollination is not nearly right the nation's agricultural is modeled on an industrial paradigm where the manufacturing flow of crop production continually stumbles over the ill-adapted and expensive handicraft component of hive-based pollination. Yet the migrating honeybee hive is the most successful commercial pollination system in the United State despite all of its drawbacks because there is no significant alternative.

There is a second much smaller insect-based commercial pollination system that utilizes the solitary bee for production of a very few commercial crops. Solitary bees are of the same Hymenoptera order as honeybees, but represent considerably more biological diversity as they have adapted to many widely varying pollination requirements. Solitaries are represented by some 3500 species in North America alone and over 25,000 worldwide compared to only seven species of honeybees of which only two are used commercially. The solitary differs radically from the honeybee in that they have neither a social structure nor a hive. Instead each female mates, builds her own nest in a cavity, provisions it with food, lays her own eggs, and dies all in the space of a few weeks time (Batra, 1984; Free, 1993). A few solitaries have been studied extensively to determine how they might be utilized as crop pollinators (Torchio 1987, 1991). Some of those studied include the mason bee (*Osmia lignaria*), hornfaced bee (*Osmia cornifrons*), alfalfa leafcutter bee (*Megachile rotundata*), alkali bee (*Nomia melanderi*), and the fuzzyfoot bee (*Anthophora pilipes*). A wide variety of techniques and trials have been conducted to ascertain their effectiveness for commercial applications. Mason bees have proven to be a particularly good pollinator of almonds in the United States (Torchio, 1981, 1991; Batra 1982). Mason and hornfaced bees have also proven a superior pollinator of apple orchards (Kuhn and Ambrose, 1984; Torchio, 1985, 1987). Additionally the fruits pollinated by Osmia have more fully developed seeds, which provide more hormones and resulting flavor, and a better shape (Torchio, 1987). In Japan hornfaced bees have been used commercially for pollination of fruit trees for many years. In Denmark the hornfaced bee has been used to pollinate greenhouse crops. Many solitaries have proven exceptionally good pollinators, far superior to the honeybee in percentage of blossom sets, speed of sets, and overall crop benefit.

The most commercially successful solitary pollinator is the leafcutter used in alfalfa seed production in North America. The problems faced by the leafcutter and mason bees are illustrative of those faced by solitaries introduced as an alternative pollinator for honeybee (Peterson et al., 1992; Griffin 1993). Nearly all the problems that prevent the solitary from becoming an effective commercial pollinator stem from its life cycle survival strategies. Most solitaries do not have gregarious nesting sites but instead seek out obscure, widely spaced cavities suitable for nests to evade the numerous predators and parasites that feed on their eggs and foodstuffs. This hiding and dispersal technique also minimized the spread and contamination by fungi and pathogens. Those solitaries with gregarious nesting habits typically have very short flight ranges and nest in relatively inhospitable environments such as the alkali flats of the alkali bee (Buchman and Nabnan, 1996). Few or no natural pests and pathogens existed in these remote, relatively sterile, isolated environments. Whether alone or in isolated colonies the solitaries were in balance with their few natural diseases and pests until agriculture disrupted their nesting sites and alien insects and pathogens entered their domains. Those solitaries which do exhibit a gregarious nesting habit—such as the leafcutter and mason bee—and are lured into small areas by artificial nesting sites so they may be managed are plagued by these natural and introduced forces which advantage themselves of such unnaturally high concentrations of easy prey. For example, the fungus *Ascosphaera aggregata* produces a chalkbrood disease specific to Megachilidae. The rate of infected larvae dead before reaching maturity can sometimes reach colony losses of 50% to 100% from year to year. Various management practices utilizing disposable nesting materials and powerful fumigants are used to treat this common pathogen (Goerzen, 1992; Mayer, 1988, 1990). Mason bees are similarly afflicted by another fungus *Ascosphaera torchioi* (Torchio, 1992). A second important problem solitary management faces is parasitism and predation. Some eight parasitic species and twenty-eight predator or nest destroyer species infest leafcutters or their nest sites; (Waters, 1980). Near total loss of a leafcutter colony can result form a heavy infestations of such opportunistic feeders from the genera of Pteromalus, Monodontomerus, Tetrasttichus and Melittobia. The mason bee experiences particularly heavy depredation by the *Stelis montana* bee and tiny Chalcid wasps, both of which lay their eggs in the mason's nesting site and heavily parasitizes the developing larva. Since the propagation rate of these parasitoids is typically many times that of the solitaries, managed clustering of nesting sites even with substantial efforts to control parasites and predators usually results in a total loss of a colony in closely packed nesting holes the following years. A third problem is the relatively few progeny solitary bees produce. The honeybee queen, protected and nurtured by the hive society, can produce thirty thousands egg a season whereas the solitary mason bee female only produces perhaps thirty, the leafcutter in field conditions about fifteen. The loss of even a few solitary eggs has a major impact on the next season pollination cycle and because of the sealed cocoon it is very difficult to determine how many viable adults will emerge for pollination. These problems are at the core of why solitaries have not found a major role in commercial crop pollination. Simply stated, their numbers fluctuate so greatly from year to year and place to place the can not be relied upon even under current best methods of management to be available and sufficient when needed. No grower can even consider this magnitude of uncontrollable risk in their operation. Alfalfa seed production has been the only commercial crop where a solitary has proven successful because honeybees are ineffectual pollinators of alfalfa whereas leafcutter bees have proven to be one of the very few species undeterred by the unusual tripping mechanism found in the alfalfa flowers. Due to this unique factor alone the extra care and expense required to manage leafcutters for greatly enhanced alfalfa seed production has proven justifiable. Unfortunately, the leafcutter has proven to be an ineffectual pollinator of any other significant crop and the mason bee has failed to reliably propagate for commercial purposes. All other solitaries share one or more of these or similar faults for similar reasons. Solitary pollination has not found any other significant commercial crop where the expense necessary for reliable, timely delivery of sufficient numbers of solitary pollinators has been lower than existing costs for the comparable process of migratory honeybee pollination.

By far the most significant expense element in producing solitary pollinators has been the costs associated with their successful propagation. A variety of techniques have been utilized in the past but they are all variations on a single common propagation method used to establish a form of pollinator management—providing an open artificial nesting site to collect solitaries for the next pollinating season. By attracting free-ranging (wild) solitaries to a open artificial nest in high-density numbers in some form of device from which the cocoons can be removed for use elsewhere, a system of solitary pollination has proven economically possible as demonstrated by the leafcutter and alfalfa seed crop. Several United States patents have well established the art of open artificial nest propagation for free-ranging (wild) solitaries. An early patent disclosed a simple layering of grooved wooden blocks held together by a bolt (Barber U.S. Pat. No. 3,936,894). A more practical design utilizing individual waxed paper tubes based on an old Japanese country custom utilizing bundled reeds followed (Norman, U.S. Pat. No. 4,365,372). More efficient designs for cocoon recovery based on an unwinding spiral nest configurations soon were issued (Weiderrich U.S. Pat. Nos. 4,293,966 and 4,319,371; Youssef U.S. Pat. No. 4,491,994). Disposable and mobile nesting box designs have been claimed in the most recent art (Pederson U.S. Pat. No. 4,628,558; Norman U.S. Pat. No. 4,716,609; McCarthy U.S. Pat. Nos. 4,765,007 and 5,591,063; Trafford U.S. Pat. No. 5,403,226; Mills U.S. Pat. No. 5,618,220). These patents represent the current state of U.S. patent art and all share the common feature of capturing the progeny of free-ranging (wild) solitary bees so the next generation of emerging adults can be used for crop pollination. A common practice now in use employs clusters of individual paper tubes to facilitate removal of nested cocoons. These tubes are bundled for placement in permanent sheds or mobile wagons located in the fields. Following the nesting season the tubes are removed from the field, opened, the cocoons obviously parasitized or diseased or dead discarded, and the few remaining solitaries kept and stored. The kept cocoons contain prepupae or imagoes in diapause and in this form they are sold by the liter or gallon to growers and providers of pollination services (Peterson et al, 1992). Because the condition of the solitaries inside any batch of unopened cocoon is unknown as to the sex ratio (only females are effective pollinators), viability due to disease or predation, and other health concerns such as fungi, samples are submitted for analysis to qualified fee-for-service laboratories such as the Canadian Cocoon Testing Center (Murrell, 1997). Given the magnitude of disease and predation among open artificial nesting no grower can afford not to have an offering of pollinating solitaries certified for quality. The most significant category of loss in raising solitaries in this manner is associated with the control of parasites, diseases, and predators. Effective control of this loss factor is a key economic component in rearing sufficient numbers of healthy solitaries and other pollinating insects so they can be reliably employed as cost effective crop pollinators.

While no closed system for rearing pollinating insects is known in prior art insect propagation technology is widely available and some patented for other purposes. Over fifteen United States patents have been issued for various apparatuses and methods in the last twenty-five year alone. Nearly all these patents put forth methods of producing insect eggs and larvae for propagation of parasitic insects, diseases, or specific insects. An early representative patent of this group (Andreev U.S. Pat. No. 3,893,420) describes capturing host eggs on a net substrata as food for parasitic insects thereby increasing the parasites numbers for use in controlling agricultural pests. A following patent (Voegele U.S. Pat. No. 4,411,220) utilized a pit and slate means for a similar purpose, producing hosts for parasitization by predatory trichogrammidae. A method for mass rearing of fruit flies (Vargas U.S. Pat. No. 4,594,964) introduced the concept of oviposting into small tubes that were flushed out with water whereby the eggs are collected. Next, a conveyor belt moving through a wasp cage upon which host eggs are inoculated with parasitic eggs was disclosed (Pizzol U.S. Pat. No. 4,765,274). More recent designs for propagating insect diseases and eaters, specifically entomopathogens and entomoparasites, made broad design and method claims all specifically concerned with producing of one or both of these objectives (Carr U.S. Pat. No. 5,113,799; Carr U.S. Pat. No. 5,178,094). The novel element of self-regulating larval spacing incorporated in an old design was advanced most recently (Hughes U.S. Pat. No. 5,351,643). None of these insect propagation patents nor any other known source describes production of pollinating insects by any techniques beyond those already detailed for the propagation of solitary bees.

SUMMARY OF THE INVENTION

The present invention provides a method for mass production of pollinating insects and their timely delivery among entomophilous plants for the pollination of a crop. Major process elements of the invention may be summarized as comprising the following important steps:

1. The establishment of rearing unit for pollinating insects which is isolated from insect viruses, bacteria, fungi, predation, and parasites;
2. The supply and conditioning of a diet medium upon which to rear pollinating insect larva;
3. The sowing of pollinating insect eggs on the diet medium, accomplished without contact with free-ranging (wild) pollinating insects;
4. The controlled storage of pollinating insects in various stages, including diapause; and,
5. The timely distribution of sufficient numbers of pollinating insects among plants at an appropriate time to produce a pollinated crop by pollination activity.

This invention of a new and useful method with applications to commercial insect pollination is a departure from both the common honeybee hive system and the more limited solitary bee system. Three of the principle distinctions are:

1. Isolation of the rearing environment from free-ranging adult insects, such isolation even extending to the exclusion of adults from involvement with nest building, food provisioning, and oviposting of ova by in vitro means;
2. Elimination by complete environmental control of destructive diseases, predators and parasites which naturally prey upon on the pollinating insects being reared; and,
3. Utilization of completely disposable pollinating insects that following their pollination function die without adversely impacting the ecology, avoid the costs of recovery, and negate any need for storage until the next season.

This invention details an insect pollination method that all but eliminates the field operation problems of the other two systems. By creating a manufacturing system producing a product (pollinating insects) all the advantages and efficiencies normally associated with such operations are secured. In a building used for large-scale propagation contamination can be controlled growing conditions maintained at optimum levels, quality diet made abundant, and a high degree operational efficiency maintained while substantially lowering per unit costs and vastly increasing the quantity of production. This invention also discloses the advantages of significantly smaller field units that substantially lower costs and reduces resources needed for distribution. For example, a typical honeybee hive placed for pollination weighs about 37 kilograms (81 pounds) and is about 0.25 cubic meters in volume (9 cubic feet). Each field board unit used in this invention has the equivalent pollinating strength of one honeybee hive, this board weighs about 0.3 kilograms (12 ounces) and is about 0.0015 cubic meters in volume (0.07 cubic feet). The field boards are 123 times lighter and 128 times smaller than the equivalent hive; the magnitude of these reductions is reflected in lowering the amount of materials needed, the cost of transportation required for distribution, and the resources needed to move the field boards into optimum field locations for effective pollination. Similar magnitudes of advantage exist in the industrial techniques of rearing pollinating insects offered by this invention.

It is therefore an object of this invention to provide an industrial-scale method for rearing pollinating insects and their subsequent distribution for pollination of crops.

Another object of this invention is to provide a pollination insect rearing environment free from entomophagous or entomopathegenic agents.

Another object of this invention is to separate the adult pollinating insect from direct oviposit of ova within the rearing environment.

Another object of this invention is to provide a highly efficient, material reducing, labor saving, energy conserving, and timely distribution system whereby pollinating insects reach their designated crop locations.

Another object of this invention is to provide sufficient quantities of pollinating insects in a reliable and timely manner to assure a high fertilization rate of the pollinated crop.

Another objective of this invention is to provide disease and parasite free pollinating insects for use in the crop land and therefore provide environmental protection.

Another object of this invention is to provide disposable pollinating insects that require no further care or concern following their activities necessary to crop pollination.

These and still other objects and advantages of the present invention will be apparent from the description that follows. In the description, the preferred embodiment of the invention will be detailed. This embodiment does not represent the full scope of the invention. Rather, the invention may be employed in other embodiments that could vary widely from the descriptions of forms or materials detailed in this example. Reference should therefore be made to the claims to interpret the breadth of the invention.

DETAILED DESCRIPTION OF THE PREFERRED EMBODIMENT

The terms "insect" and "insects" as used herein refers to any animal of the class Insecta, including but not limited to the orders of Hymenoptera (bees), Coleoptera (beetles) and Diptera (flies), all of which include species and subspecies that can pollinate plants by their activities such as found in the families of Megachilidae, Halictidae, Andrenidae, Apidae and the tribe Bombini.

The term "pollinating insects" as used herein refers to any insect that by its actions can pollinate at least one entomophilous plant at an appropriate time; this term is specifically intended to include any and all animal species and subspecies which are or would be classified by accepted taxonomic practices as being a member of the order Insecta and are capable of performing a pollinating function.

The term "rearing environment" as used herein refers to any enclosed controlled environment such as rooms within which the pollinating insects are reared; this term is specifically intended to note such a controlled environment wherein all entomopathogens and entomoparasites such as insect viruses, bacteria, fungi, parasites and predators are both absent and excluded by all and any means necessary to achieve and maintain the controlled environment.

The term "pollinated crops" as used herein refers to any plant part, product, or feature deemed to have economic, aesthetic, or genetic value resulting from or in any manner associated with fertilization derived from pollination action involving an insect.

This invention discloses a method of crop pollination wherein pollinating insects are reared on an industrial-scale with manufacturing methods and are subsequently distributed among plants so pollination takes place and a pollinated crop results. While a vast number of pollinating insects can be utilized in this method, all achieving the same general result of pollination of the same or varied pollinated crops, by way of example the mason bee (*Osmia lignaria*) is used herein to illustrate the method in detail. The alfalfa leafcutter bee has a different life cycle from the mason bee as does that of the beetle (*Elaeidobius kameruaicus*) used for pollination of oil palms in the tropics (Proctor, 1996). A simple walk-thru of the method using the mason bee as the pollinating insect will illustrate the method's practice in one embodiment. At the end of the walk-thru the unique advantages of the method over the prior art and other methods will be described. The apparatuses employed in the walk-thru are only for illustrative value and many extreme variations within the scope of the method are contemplated. Many of these variations reflect the specific requirements of a specific pollinating insect being reared. For example, some beetles due to their size require more space and substantially different diet and environmental controls. In other cases, some flies would be collected for distribution while in a larval stage before reaching the adult imago form. All insects utilized by this method however begin with a rearing unit and an ovum. And it is with the ovum of the mason bee and the rearing unit that the walk-thru begins.

The rearing unit used for mason bees is a simple shallow plastic tray capable of being thoroughly cleaned and sterilized by autoclaving or commercial disinfectant. Each tray has about 0.3 square meters of surface with raised edges of two cm, they have the overall appearance of common cafeteria trays with their flared upper edges used for horizontal hanging. These rearing trays are housed within a room where temperature, humidity, airflow, light, and all other environmental factors are controlled so as to benefit the rearing of the pollinating insect, in this example the mason bee. A suitable rearing environment for mason bee ovum and larva is a temperature of 29° C., 75% RH, 0:24 LD photoperiod. HEPA filters, positive airflow, chambered entrances, disinfectant washings and other common practices are used to establish and maintain a clean rearing environment to protect the rearing units and their developing insects from damaging or lethal entomological viruses, bacteria, fungi, parasites, or predators. All equipment, material and personnel entering the clean rearing environment are suitably disinfected or appropriately clothed to prevent any form of contamination. The rearing trays used in the early rearing steps are completely isolated from any entomological contamination and this care consequently protects the mason bees from damage.

A diet mixture is placed in the rearing trays to a depth of about two millimeters. An adequate diet for the mason bee has been found to be a refined blend of a commercial formulation consisting of soy flour, brewers yeast, sugars and sterilized water. This diet material is formed into the bottom of the tray where a matrix of shallow dimples formed on one-centimeter centers is impressed into the upper surface of the diet medium. The diet is an aseptic replication of pollen proteins and nectar sugars a mason bee uses to naturally provision a wild nest. Approximately 3000 fertilized mason bee ova in a suspension of sterile water and fortified MEM (Minimum Essential Medium) are flooded across the diet surface, the tray is rotated so individual ova settle into individual dimples in the diet medium. The solution is absorbed by and then evaporated from the diet medium. As soon as each tray is sown with mason ova it is placed in a wheeled grow-rack, hung in place by the tray's flared edges in a manner commonly found in the return racks for trays found in cafeterias. A grow-rack is two meters high and contains 120 trays stacked in two columns. When full a typical rack contains some 360,000 mason bee ova and occupies less than one square meter of floor space. Upon being filled with rearing trays a grow-rack is moved to a floor location where it remains undisturbed for about 45 days. One exception to this storage time would be when the tray containing larva at an appropriate development phase is taken for exposure to gamma radiation for the purpose of producing sterile imagoes. Fifty racks fit in a typical rearing room measuring six by ten meters, one such room contains about 18 million mason bees.

During this period of the first 45 days (1–45 days, time line) a transformation takes place on the rearing trays in the dark. Within a few hours of being sown the mason bee ovum begin to undergo cell division. From the one-cell ova many specialized cells begin to develop by means of mitotic division. First of the specialized cells to form are those necessary to create a primitive mouth structure that quickly attaches itself to the diet medium and, as soon as the equally primitive digestive tract is formed begins to feed. Within about four days (1–4 days, time line) a larva has developed from the ova and begins to feed quickly. In about thirty days—depending on the subspecies and any slight lowering of the ambient temperature made to retard growth—the feeding stops and the larva rests (1–30 days, time line). After a couple of days of quiescence the larva begins to twist about spinning a cocoon about itself that will protect it during the upcoming time of metamorphosis that results in the transformation of the larval to an imago. The cocoon is typically completed in one day (32 day, time line). It is brown when cured, tough and about the size of a small elongated bean. A second period of rest lasting approximately 30 days now begins (32–61 days, time line). After resting within the cocoon the larva now undergoes metamorphosis wherein the entire body undergoes a cellular reorganization and substantial cell specialization to form the body parts of the adult form. Mason bee metamorphosis is complete in about 40 days (61–101 days, time line). In order to optimize floor space utilization and maintain an efficient assembly line work flow the cocoons are removed from the trays in the grow racks at about 45 days from when the ova were originally sown. The cocoons are placed in clean cartons for high-density storage under the same environmental conditions as the rearing trays until metamorphosis is completed. The rearing trays are cleaned before reuse, another diet medium put in place, another batch of ova seeded and another grow-rack loaded for rearing another generation of mason bees. By this assembly line approach six generations of mason bees can be created for every unit of floor space each year.

The mason bee cocoons now in high-density storage cartons are undergoing metamorphosis. At the end of this transformation the cartons are moved to another clean rearing environment in a cold storage room where the environment is maintained at 4–6° C., 50% RH, 0:24 LD photoperiod. Temperatures in this range initiates diapause in mason bees. Diapause under these conditions lasts up to twelve months with a 5–8% mortality rate. Alternatively, diapause can be broken after the first month by choosing to raise the ambient temperature to awaken the mason bees. Typically, mason bee cocoons are kept in diapause four to ten months before being packaged for field distribution.

Mason bee cocoons are packaged in field boards for transportation to orchards, gardens and fields. The field boards measure 20×25×4 cm, are made of recycled fiber and have a fiber cord for attachment. On the front of the field board are six formed channels each 6 mm deep. At least 130 cocoons are placed in these channels and a tan paper sheet is affixed to the front surface of the field board to cover and secure the cocoons in place. Based on a number of credible field trails conducted by Torchio and others, approximately 130 female mason bees in a typical orchard setting for such crops as apples and almonds are the pollinating equivalent of one honeybee hive (Torchio 1985, 1987, 1991). The completed field board weighs approximately 0.3 kilograms and has a volume of 0.0015 cubic meters. On the reverse side of the field board is a matrix of 24×34 holes on 7 mm centers, each hole is 5 mm wide and 3 cm deep. The 816 matrix holes that are open on the reverse surface are designed to provide a local nesting site for emerging mason bees that chew their way out through the front paper when they emerge from diapause. The matrix also provides a means of visually monitoring the success and progress of the pollination activity. Further, the field board is designed to self-destruct through weathering over time so that the nested mason bee larva and cocoons are unprotected and subsequently expire. This is done to control disease, parasite and predator propagation in the field and to protect the local environment from destabilizing influences. Emergence from diapause is controlled by the ambient temperature which surrounds the cocoon, a continual temperature above approximately 12°–15° C., 50–75% RH breaks mason bee diapause in about eight to ten days. Lower or fluctuating temperatures can retard the emergence, higher temperatures can slightly advance the timing. A drop to cold storage temperatures can return the mason bee to diapause if the done in the first few days. When the temperature has remained elevated a sufficient time to break diapause the mason bee imago within the cocoon chews through the cocoon wall and out through the paper covering to emerge. The bee is oriented to the paper as an exit route due to the relatively greater warmth and light originating from that surface. Once emerged the mason bee begins its pollination activity, leading to flower fertilization, resulting in crop pollination, culminating in production of a crop.

A key feature of this pollination method is the economy, ease of use, and controllability of the field boards. At the plant the filled field boards are packed in shipping cartons, ten to a box for a total shipping weight of about 4.5 kilograms (10 pounds). The cartons are shipped directly to growers by commercial delivery services like United Parcel Services, Federal Express or direct carriers for major growers, cooperatives and associations. All shippers accept diapausing insects with adequate time deliver guarantees. The diapausing mason bees within their cocoons are impervious to normal shipping conditions. Upon receipt by the grower the cartons are opened for placement in the field if the bloom conditions merit immediate dispersal. Alternatively, if the bloom is delayed or the cartons were received intentionally early to simply have on hand when needed, the cartons are stored in a cool environment until conditions warrant dispersal. The grower has complete control of when and where the field boards are to be placed. Given the size and weight of the boards the grower can walk the boards to optimum locations regardless of muddy conditions, narrow lanes, or mass plantings. For example, an apple orchardist has 20 acres in which he needs to distribute 60 field boards, three per acre or 390 mason bees. Intermittent late warm rains have turned the orchard's alleys into mud but the same rains are also bringing on a strong bloom. Six cartons of mason bees weighing ten pounds each are walked by one man into the orchard and optimally distributed among the apple trees in one afternoon. There are no mired trucks or forklifts to recover, the tree roots are not damaged by deep ruts in the alleys, hives have not been ineffectually set at the margins of the orchard, and the grower's worry and disappointment over uncontrollable circumstances has been completely avoided. A couple of weeks later the corollary scenario to this event occurs when the honeybee hives need to be retrieved from the orchard. The same access concerns reoccur with the hives, but with the field boards there is no retrieval necessary. The mason bees and their field boards are disposable, they both have performed their functions and both now die or disintegrate through weathering to mix with the soil.

Solitary bees like the mason bee work quickly to pollinate while staying close to their original base. Since they have no social system there are no scouts to locate far away caches of rewarding wild flowers. The solitary energy schedule is too strict, they can not afford to explore. They do not skip over blooms looking for higher returns further away. This behavior leads to a highly desirable pollinating trait of repeated, quick, vigorous visits to blossoms to scour out the last bit of nutrition and incidentally heavily pollinate at the same time. Solitaries like the mason bee will set an acre of orchard blossoms in a matter of days instead of weeks needed by the honeybee. This activity level has many immediate benefits (earlier spraying of pesticides, less risk of weather damage to blossoms, etc.) but one advantage that is not recognized immediately occurs at harvest. By having the fruit set occurring closer together an entire tree can be harvested of mature fruit in one pass and thus saving considerably on setup time and similar harvesting logistics. Another type of advantage offered by adequate numbers of solitaries being released to pollinate occurs with the sunflower crop. Again the solitaries can pollinate in a matter of days, much faster than honeybees. This rapid pollination produces a larger crop in the case of sunflowers, the key factor in this increased production is that when a sunflower floret is pollinated it immediately closes to begin production of the seed. Among sunflowers there is a highly destructive pest called the sunflower moth that arrives a few days after the florets open to lay its eggs in these same blossoms where they eventually hatch and eat the seed. The longer the florets are open (not pollinated) the greater the crop damage. A quick set by solitaries substantially reduces crop damage from this pest. And with a quicker pollination set the grower can spray earlier to control other destructive pests. Solitaries such as the mason bee offer a viable alternative to the honeybee hive system when they are produced in sufficient numbers and can be reliable distributed when and where needed. The invention herein disclosed is a method of crop pollination by insects that provides a viable alternative pollination system to the honeybee hive and goes further to secure advantages not possible with the hive system.

The disclosed method herein is a superior departure from the dominant honeybee hive system used for commercial pollination. The hive pollination system is an awkward lash-up of an ancient handicraft created to produce honey and now forced into service to provide pollination. It is an ill-suited service component in an agriculture system built on an industrial model. Problems of disease deprivations, transportation hitches, bloom timing, field distribution, conflicting contract obligations, operator's liability, grower's damages, rising costs, and a host of like concerns underscore just how badly the hive system fulfills its role. All these problems can be traced back to the simple fact the hive system has none of the attributes of a proper industrial subsystem. The method disclosed by this invention has those industrial attributes:

1. Centralized quality control of production;
2. Efficient assembly lines producing on-demand product;
3. High volume output of standardized products;
4. Independent point-to-point lines of distribution;
5. Full grower utilization control; and,
6. End-use product incorporation.

Each of these attributes of a manufacturing subsystem is an inherent element of the disclosed invention and missing from the hive system. Disease and parasites prevent the free-ranging solitary method from every becoming a viable general pollination system because it lacks the ability to reliably produce adequate numbers of pollinators for use when and where they are needed. The new pollination method herein described overcomes these problems by centralizing production in a manufacturing setting which makes possible isolation practices to control disease and parasites. This element is unknown in and a distinct improvement over the open-field, free-ranging nesting system of the prior art as known through literature and patents. This isolation element, when coupled with the other methods steps of rearing and distribution, creates a viable and superior system for general crop pollination by insects.

In the larger art of general insect propagation there is no known disclosure of the method described by this invention for the mass production of pollinating insects. Portions of the rearing techniques (trays, food, harvesting) in this method are common practices in the ancient art of sericulture and the daily operations of modern insectaries, but as incorporated within a new method for production and distribution of pollinating insects to pollinating crops these practices become part of a new art. Nearly all known prior art exclusively pursues the propagation of insects as a means to produce viruses, as a food source for other predatory insects, or genetic research. No known prior art in the literature or patents discloses propagation means as described herein for pollinating insects as an element within a method for crop pollination by insects.

The primary goal of this invention is to simply establish a new, more efficient method for the commercial pollination of crops by insects.

Throughout this application various publications are referenced. The disclosures of these publications in their entireties are hereby incorporated by reference into this application in order to more fully describe the state of the art to which the invention pertains.

Although the invention has been described in considerable detail in the foregoing, it is to be understood that such detail is solely for the purpose of illustration and that variations can be made by those skilled in the art without departing from the scope and spirit of the invention except as set forth in the claims.

What is claimed is:

1. A method of crop pollination by insects comprising:
   a. providing a rearing unit located within an appropriate rearing environment for pollinating insects;
   b. isolating said rearing unit from substantially damaging or lethal entomological viruses, bacteria, fungi, parasites, or predators;
   c. provisioning said rearing unit with an appropriate diet medium;
   d. sowing in vitro isolated ova of said pollinating insects on said diet medium;
   e. incubating said ova for a duration of time adequate to rearing said pollinating insects;
   f. collecting insect imagoes from said rearing unit; and, g. distributing said insect imagoes among entomophilous plants at an appropriate time whereby said pollinating insects pollinate to produce a pollinated crop.

2. The method of claim 1, wherein said insects are of the order Hymenoptera.

3. The method of claim 2, wherein said insects are solitary bees.

4. The method of claim 2, wherein said insects are social bees.

5. The method of claim 2, wherein said insects are of the family Megachilidae.

6. The method of claim 2, wherein said insects are of the family Halictidae.

7. The method of claim 2, wherein said insects are of the family Andrenidae.

8. The method of claim 2, wherein said insects are of the family Apidae.

9. The method of claim 2, wherein said insects are of the tribe Bombini.

10. The method of claim 1, wherein said insects are of the order Coleoptera.

11. The method of claim 1, wherein said environment employs temperature as a means for controlling rate of development of said pollination insects.

12. The method of claim 1, wherein said distributing is by means of an appropriate container conveying said pollinating insects.

13. The method of claim 12, wherein said container utilizes temperature as a means for timing emergence of said pollinating insects for said crop pollination.

14. The method of claim 12, wherein said container substantially distengrates by means of weathering within a determined period of time.

15. The method of claim 14, wherein said container wastes progeny of said free-ranging pollinating insects by destruction of said container.

16. The method of claim 12, wherein said container provides structural means to induce ovum laying of free-ranging pollinating insects.

17. The method of claim 1, wherein said pollinating insects are exposed to sterilizing radiation at an appropriate time and in sufficient amount to induce sterilization in said imagoes.

18. A method of crop pollination by insects comprising:
a. providing a rearing unit located within an appropriate rearing environment for pollinating insects;
b. isolating said rearing unit from substantially damaging or lethal entomological viruses, bacteria, fungi, parasites, or predators;
c. provisioning said rearing unit with an appropriate diet medium;
d. sowing in vitro isolated ova of said pollinating insects on said diet medium;
e. incubating said ova for a duration of time adequate to rearing said pollinating insects; and,
f. distributing said pollinating insects among entomophilous plants at an appropriate time whereby said pollinating insects pollinate to produce a pollinated crop.

19. The method of claim 18, wherein said environment employs temperature as a means for controlling rate of development of said pollination insects.

20. The method of claim 18, wherein said distributing is by means of an appropriate container conveying said pollinating insects.

* * * * *